United States Patent [19]

Giuliani et al.

[11] Patent Number: 4,907,857

[45] Date of Patent: Mar. 13, 1990

[54] OPTICAL FIBER DISTRIBUTION SYSTEM FOR AN OPTICAL FIBER SENSOR

[75] Inventors: David Giuliani, Mercer Island; Robert A. Gutcheck, Bothell, both of Wash.

[73] Assignee: Abbott Laboratories, Abbott Park, Ill.

[21] Appl. No.: 366,762

[22] Filed: Jun. 14, 1989

Related U.S. Application Data

[63] Continuation of Ser. No. 224,442, Jul. 25, 1988, abandoned.

[51] Int. Cl.[4] .......................... G01D 5/30; G01D 5/34; G01J 5/42
[52] U.S. Cl. .......................... 350/96.29; 250/227.23; 250/231.10; 356/320
[58] Field of Search .......................... 350/96.10, 96.29; 250/227, 231 R; 356/40, 41, 320

[56] References Cited

U.S. PATENT DOCUMENTS

| | | | |
|---|---|---|---|
| 4,249,076 | 2/1981 | Bergstrom et al. | 250/231 R |
| 4,299,487 | 11/1981 | Sengoku et al. | 356/320 |
| 4,342,919 | 8/1982 | Brogardh | 250/577 |
| 4,356,396 | 10/1982 | Ruell et al. | 250/227 |
| 4,356,448 | 10/1982 | Brogardh et al. | 250/231 R |
| 4,378,496 | 3/1983 | Brogardh et al. | 250/227 |
| 4,433,238 | 2/1984 | Adolfsson et al. | 250/227 |
| 4,514,860 | 4/1985 | Adolfsson et al. | 455/612 |
| 4,523,092 | 6/1985 | Nelson | 250/227 |
| 4,529,875 | 7/1985 | Brogardh et al. | 250/227 |
| 4,554,449 | 11/1985 | Taniuchi et al. | 250/227 |
| 4,594,504 | 6/1986 | Coursolle et al. | 250/227 |
| 4,599,711 | 8/1986 | Cumo | 367/141 |
| 4,703,175 | 10/1987 | Salour et al. | 250/227 |
| 4,705,354 | 11/1987 | Ulrich | 350/96.29 |
| 4,760,250 | 7/1988 | Loeppert | 250/227 |
| 4,792,689 | 12/1988 | Peterson | 250/458.1 |
| 4,799,797 | 1/1989 | Huggins | 356/345 |

FOREIGN PATENT DOCUMENTS

2913545 10/1979 Fed. Rep. of Germany ...... 356/320

OTHER PUBLICATIONS

"Optical Fluorescence and its Application to an Intravascular Blood Gas Monitoring System", IEEE Transactions on Biomed. Engineering, by Gehrich et al., vol. BME-33, No. 2, pp. 117-132, Feb. 1986.

Primary Examiner—William L. Sikes
Assistant Examiner—Akm E. Ullah
Attorney, Agent, or Firm—Christensen, O'Connor, Johnson & Kindness

[57] ABSTRACT

A device for distributing signals within a sensor system used for monitoring the presence of a specific analyte in a composition by means of an analyte-sensitive indicator molecule is disclosed. The sensor system includes a signal-generating component, a single-fiber sensor tip that houses the indicator molecule and a signal-measuring component. In one embodiment, the signal-generating component generates a first optical signal of a wavelength that is sensitive to the indicator molecule, and a second optical signal of a wavelength that is predictably altered by the indicator molecule. The distribution system includes lengths of optical fiber, a dividing connector, a mixing connector, a transmitting connector and a tip connector. The dividing connector connects at least three intermediate fibers to the signal-generating component to receive intermediate signals. The mixing connector connects a mixing fiber to the intermediate fibers to receive the intermediate signals and blend them into a single mixed signal. The transmitting connector connects a transmitting fiber to the mixing fiber to thereby receive a portion of the mixed signal, and connects a comparison fiber to the mixing fiber to transmit a portion of the mixed signal to the signal-measuring component. The tip connector connects the transmitting fiber to the sensor tip fiber to transmit a portion of the mixed signal to the sensor tip, and connects an indicator fiber to the sensor tip to transmit a portion of the resulting indicator signal returned from the sensor tip to the signal-measuring component.

18 Claims, 3 Drawing Sheets

OPTICAL FIBER DISTRIBUTION SYSTEM FOR AN OPTICAL FIBER SENSOR

This application is a continuation application based on prior copending application Ser. No. 07/224,442, filed on July 25, 1988, now abandoned.

FIELD OF THE INVENTION

This invention relates to an optical fiber distribution system suitable for use in an optical fiber sensor system and, more particularly, for use in an optical fiber sensor system having a sensor tip made up of a single fiber and incorporating optical wavelength sensitive indicators to monitor analyte concentrations in compositions, and having distribution system monitoring capabilities.

BACKGROUND OF THE INVENTION

In recent years, optical fiber sensors, also known as optrodes, have been developed to detect the presence and monitor the concentration of various analytes, including oxygen, carbon dioxide, glucose, inorganic ions, and hydrogen ions, in liquids and in gases. Such sensors are based on the rcognized phenomenon that the absorbance or luminescence of certain indicator molecules is specifically perturbed in the presence of certain analytes. The perturbation in the absorbance and/or luminescence profile can be detected by monitoring radiation that is reflected or emitted by the indicator molecule when it is in the presence of a specific analyte. The targeted analyte is generally a part of a solution containing a variety of analytes.

Duofiber optical sensors have been developed that position an analyte-sensitive molecule in the light path of a sensor tip. The indicator molecule is typically housed in a sealed chamber whose walls are permeable to the analyte. The sealed chamber is submerged in the analyte-containing solution. The sensor tip includes a pair of optical fibers. The term "duofiber" refers to the number of fibers in the sensor tip. In comparison, a "single-fiber" sensor utilizes only one fiber in the sensor tip. In a duofiber sensor, one fiber transmits electromagnetic radiation, termed measuring signal, from a signal-generating component to the indicator molecule. The other fiber transmits the reflected or emitted light, termed indicator signal, from the sensor tip to a signal-measuring component that measures the indicator signal intensity. The configuration of the optical fibers between the signal-generating component, the sensor tip, and the signal-measuring component describes the optical fiber distribution system for the sensor system.

There are two uncommon types of sensor systems: absorption and luminescent. In an absorption system, an analyte-sensitive dye is typically housed in the sealed chamber of the sensor tip. The system operates on the concept of optically detecting the change in color of the analyte-sensitive dye. This is done by measuring the intensity of the measuring signal reflected or unabsorbed at the sensor tip and comparing it to the intensity of the original measuring signal to determine the portion of the measuring signal that was absorbed by the dye at the sensor tip. Suitable analyte-sensitive indicator molecules are known in the art and are selected based upon the particular analyte substance whose detection is targeted.

There are two major types of luminescent sensor systems: phosphorescent and fluorescent. Such systems operate on the concept of measuring the luminescent intensity or lifetime of the radiation emitted by the excitation of the analyte-sensitive molecule. The sensor irradiates the indicator molecule with light at a wavelength band corresponding to a region of analyte-dependent absorbance by the indicator molecule. Luminescent emission is measured by the signal-measuring component. The ambient analyte concentration is determined by known techniques as a function of the measured luminescent emission.

The optical fiber distribution system is an integral part of each optical fiber sensor system. The distribution system is made up of optical fibers and optical connectors. The distribution system directs the measuring signal from the signal-generating component to the sensor tip and also directs the reflected or emitted indicator signal from the sensor tip to the signal-measuring component. If the sensor is using an absorption monitoring technique, the distribution system will additionally direct a portion of the measuring signal directly to the signal-measuring component. A determination of the quantity of a specific analyte is then made by comparing the intensity of the measuring signal to the intensity of the indicator signal. As noted above, if the sensor is using a luminescent monitoring technique, the analyte concentration is determined by analyzing the emitted indicator signal over a period of time.

The efficiency and reliability of a sensor system largely depends on its optical fiber distribution system. Although current optical fiber technology may not provide a one hunderd percent signal transfer at fiber connection points, the signal reduction at optical fiber connections should be ascertainable and controllable. Variability in analyte concentration measurements that may be related to the optical fiber distribution system arise from fiber loss, fiber coupling inefficiency, fiber concentration, and response to noise, either random or periodic, produced by a variety of internal and exernal sources.

In current medical applications, it is desirable that the fiber distribution system be relatively small, flexible, and highly efficient. The size requirement becomes more crucial as in situ blood gas monitoring techniques are being developed. For example, a blood gas catheter or sensor may be inserted into and left in a patient's body for a long period of time to provide continuous monitoring of specific conditions. The catheter tip includes the analyte-sensitive indicator molecule. For the patient's comfort, the catheter tip should be as small as possible. To accommodate this desirable size characteristic, a single fiber extending to the catheter tip is desirable. The remainder of the distribution system is then sized to proportion to the catheter tip fiber for maximum efficiency.

In a single-fiber sensor system, a single optical fiber carries the measuring signal to the indicator molecule, as well as carries the reflected or emitted indicator signal from the indicator molecule. One useful characteristic of a single-fiber system is that it is reducible to nearly one-half the size of the duofiber system at the sensor tip. However, a single-fiber sensor presents problems related to the small amount of light a single fiber, as well as the related distribution system, can carry, and the ability of the system to distinguish indicator signals from measuring signals that are reflected back at imperfect fiber connections. The former problem is especially prevalent in analog-based sensors. Medical sensors are generally of this type. In analog-based sensors, the intensity of the signal produced at the sensor rather than the mere existence of the signal, as in a digital system, is significant. Each change in signal intensity that is not traceable to a constant in the distribution system will be attributed to a parameter in the monitoring process. Thus, the optical fiber distribution system must be highly predictable and reliable in order to provide useful monitoring results.

SUMMARY OF THE INVENTION

In accordance with this invention, a distribution system for a sensor system and a method of distributing signals are described. The distribution system is suitable for use in a variety of single-fiber sensor systems that have a signal-generating component for generating two signals of distinct wavelengths, a single-fiber sensor tip, and a signal-measuring component. The intensity of the first signal wavelength generated by the signal-generating component is altered by the indicator molecule in proportion to the presence of the analyte. The intensity of the second signal wavelength is predictably altered by the indicator molecule. The optical distribution system of the present invention provides greater signal magnitude as measured by the signal-measuring component, provides known signal reduction at fiber connection points, decreases the effect of noise on the monitoring process, and provides a systems operation monitor.

The present invention includes lengths of optical fiber, a dividing connector, a mixing connector, a transmitting connector and a tip connector. The optical fiber lengths are of first and second diameters, the second diameter being larger than the first diameter. In one embodiment, the second diameter is substantially equal to the diameter of the sensor tip fiber. The dividing connector connects at least three intermediate fibers of the first diameter to the signal-generating component to thereby receive intermediate signals. At least one of the intermediate signals corresponds to the first signal and at least one intermediate signal corresponds to the second signal. The mixing connector connects a mixing fiber of the second diameter to the intermediate fibers to thereby receive the intermediate signals and blend them into a single mixed signal. The transmitting connector connects a transmitting fiber of the first diameter to the mixing fiber to thereby receive a portion of the mixed signal. The tip connector connects the transmitting fiber to the sensor tip fiber to thereby transmit the mixed signal to the sensor tip, and connects an indicator fiber of the first diameter to the sensor tip to thereby transmit a portion of the resulting indicator signal returned from the sensor tip to the signal-measuring component. The intensity of the intermediate signals corresponding to the first signal is maximized at the dividing connector. The intensity of the intermediate signals corresponding to the first signal is bounded by the necessity of transmitting intermediate signals corresponding to the second signal of adequate intensity such that the intensity of the indicator signal corresponding to the second signal received by the signal-measuring component is suitable for providing distribution system information such as operation status.

In accordance with further aspects of the present invention, the relationship of the first diameter relative to the second diameter, and of the configurations of the dividing connector, the mixing connector, the transmitting connector, and the tip connector, are such that at each connector where a fiber of the second diameter is connected to a fiber of the first diameter, the fiber of the second diameter completely subtends the fiber of the first diameter.

In accordance with additional aspects of the present invention, the dividing connector connects three intermediate fibers to the signal-generating component to thereby receive signals of the first signal wavelength and connects one intermediate fiber to the signal-generating component to thereby receive signals of the second wavelength. The transmitting connector connects two transmitting fibers to the mixing fiber, and the tip connector connects two indicator fibers to the sensor tip.

In accordance with other aspects of the present invention, the transmitting connector connects a comparison fiber of the first diameter to the mixing fiber to thereby transmit a portion of the mixed signal to the signal-measuring component.

In accordance with still further aspects of the present invention, at each fiber connection point the reduction in signal intensity is known, minimized, and controllable. The amount of signal transferred at the connection is highly predictable. The number and diameter of the fibers are optimized to reduce cost and size, and to increase signal-to-noise ratio.

In accordance with still other aspects of the present invention, as an alternative to the tip connector connecting the transmitting fiber to the sensor tip fiber, the transmitting fiber may be connected to a tip fiber means for transmitting the mixed signal to the sensor tip. In one case, the tip fiber means will include the single fiber of the sensor tip. Alternatively, the tip fiber means will include an extension fiber, one end of which is connected to the transmitting fiber and the indicator fiber via the tip connector.

In accordance with still further aspects of the present invention an optical fiber distribution system is provided that is efficient and inexpensive to produce.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENTS

The optical fiber distribution system of the present invention is suitable for use in conjunction with a variety of physiological pH and blood gas concentration sensors. The distribution system is integratable into a single-fiber tip sensor system. Preferred embodiments of the distribution system will be described in conjunction with pH/PCO$_2$ absorption sensors and with PO$_2$ luminescent sensors. However, it is to be understood that the following descriptions are not meant to limit the present invention to use in conjunction with any specific sensor types.

Figure 1:
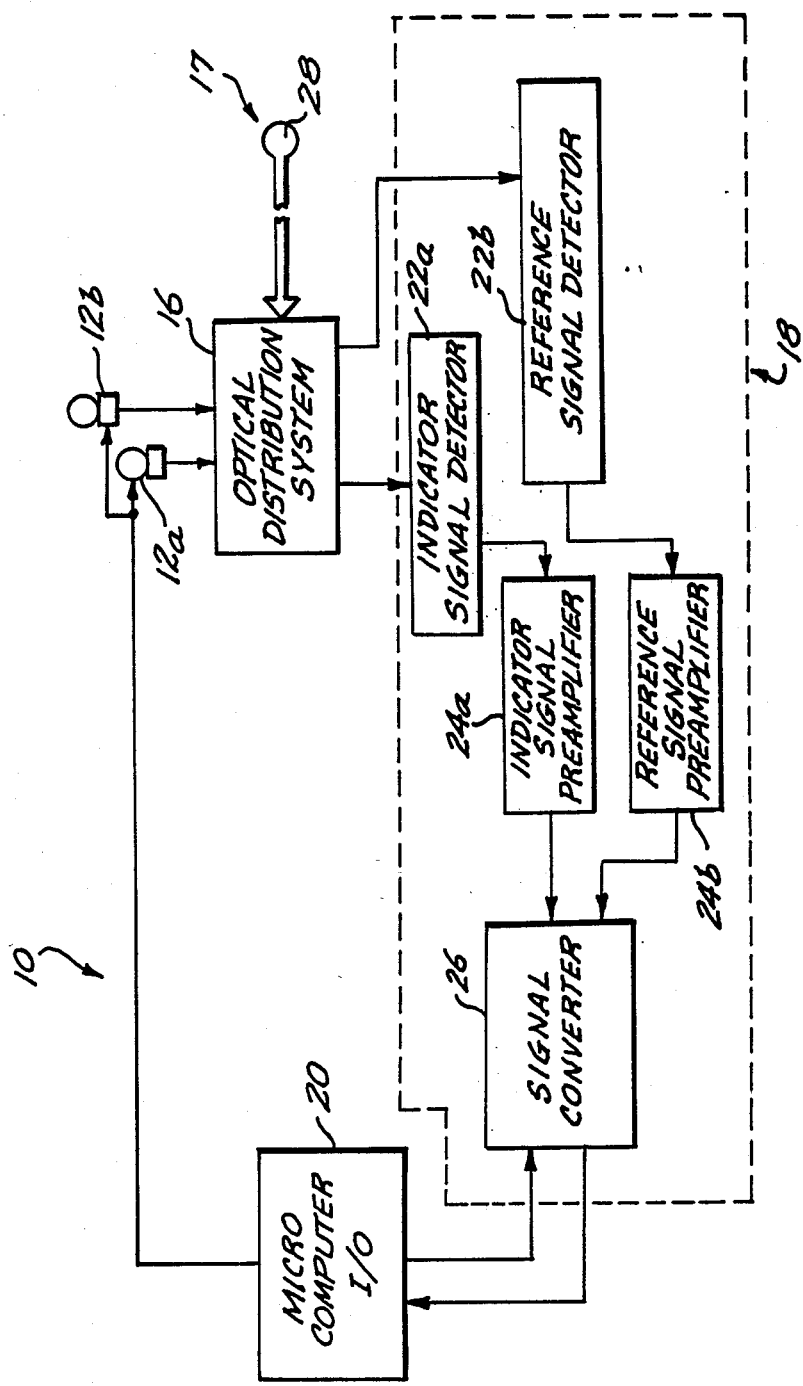
FIG. 1 is a block diagram of a representative system for measuring pH/pCO$_2$ and O$_2$, including an optical fiber distribution system in accordance with the invention.

FIG. 1 shows a representative sensor system 10 for determining the pH/POC$_2$ concentration of gaseous compositions by measuring the quenching of various sensor indicator molecules by the composition. The system 10 includes: signal-generating component 12; optical distribution system 16; sensor tip 17; signal-measuring component 18; and microcomputer 20. The signal-measuring component 18 includes: indicator-signal and comparison-signal detectors 22(a) and 22(b); indicator-signal and comparison-signal preamplifiers 24(a) and 24(b); and signal converter 26.

The system 10 provides light excitation of a pH/PCO$_2$ quenching-sensitive composition 28, such as a phenol red based composition, sequestered in the sensor tip 17. The sensor tip 17 and composition 28 are submerged in an analyte-containing solution (not shown). The signals transmitted from signal-generating component 12, preferably a pair of colored L.E.D.s 12(a) and 12(b), pass through optical fiber distribution system 16. L.E.D. 12(a) generates a signal, termed measuring signal, that is of a wavelength that will be absorbed by the indicator molecule in composition 28 in proportion to the presence of pH/PCO$_2$ in the analyte-containing solution. L.E.D. 12(b) generates a signal, termed reference signal, that is of a wavelength that is predictably quenched by the composition 28 so that the intensity of the signal reflected at the sensor tip is predictable. As the reference signal is transmitted through system 10, it is subject to known signal intensity reductions at the various component connections and at the sensor tip.

The distribution system divides the measuring and reference signals into intermediate signals and mixes those to produce a single mixed signal. The distribution system transmits a portion of the mixed signal to the comparison-signal detector 22(b) and a portion on to the sensor tip 17. At the sensor tip, the mixed signal encounters the quenching-sensitive composition.

The radiation in the mixed signal that corresponds in wavelength to the measuring signal is absorbed by the indicator molecule in proportion to the quantity of the analyte present in the analyte-containing solution. The radiation in the mixed signal that corresponds in wavelength to the reference signal is absorbed at a predictable rate by the analyte-sensitive composition. The unabsorbed or reflected signals are termed indicator signal. The distribution system transmits the indicator signal from the sensor tip to the indicator-signal detector 22(a).

The comparison- and indicator-signal detectors receive optical signals as input and output corresponding electrical signals. An example of a conventional signal detector is a positive-interface-negative (PIN) silicon component. The indicator signal is transmitted to indicator preamplifier 24(a), and the mixed signal is transmitted to comparison-signal preamplifier 24(b). The preamplifiers 24 transmit the amplified signals on to the signal converter 26, which converts the signals from analog to digital. The signals are then input into the microcomputer 20, which controls the sensor's operation and acts as an input/output device for the sensor.

The microcomputer analyzes the signals received from the signal-measuring component 18 to monitor the presence of the analyte as well as the distribution system operation. The measuring and reference signals in the mixed signal, and the reflected measuring and reference signals in the indicator signal are all distinguishable by their respective wavelengths at the signal-measuring component 18. The signals representing the measuring and reference signals are isolated by filtering. Alternatively, if the reference and measuring signals are generated at distinct time intervals, then the signals are isolated by time differentiation. The microcomputer compares the intensity of the measuring signal received at the comparison component to that received at the indicator component to determine the quantity of the analyte in the solution being monitored. The microcomputer also compares the intensity of the reference signal received at the comparison component to that received at the indicator component to determine whether the distribution system is operating accurately.

By replacing the sensor tip sequestering a pH/PCO$_2$ quenching-sensitive composition 28 with a tip sequestering an PO$_2$ luminescent-sensitive composition, such as a porphyrin based composition, the system 10 acts as an PO$_2$ monitoring system. In a phosphorescent monitoring system, only a single signal source is required. No reference signal need be generated or transmitted through the system because of the nature of the phosphorescent measuring procedure. The phosphorescence is an inherent quality of the sensor that is fixed by the dye matrix. The decay time for any given PO$_2$ quantity is unique. Thus, the intensity of the measured or indicator signal does not affect the measuring process. Thus, no reference signal is necessary to monitor distribution system operation to guard against unexpected signal intensity reduction due to distribution system malfunctions.

The optical fiber distribution system 16 operates in the same manner as described above. At the sensor tip, the excitation caused by the measuring signal causes the luminescent-sensitive composition to emit radiation, identified as an indicator signal. The indicator signal includes radiation in a wavelength band corresponding to the emission caused by the measuring signal. The indicator-signal detector 22(a) includes a wavelength-isolation component to detect and isolate the emitted radiation. An example of a wavelength isolation component is a spectral filter that isolates the spectral region of interest.

In the microcomputer, the time decay of the emitted signal in the wavelength band corresponding to the excitation caused by the measuring signal is measured. One method of measuring the time decay of the signal is to consider a division of the signal as a function of time and compare the ratio of the two parts as a function of time. This comparison produces an indication of the presence of the analyte in the solution being monitored. Although they are not utilized, the presence of the comparison component of the signal-measuring component and of the aspects of the distribution system related to the transmission of a reference signal do not affect the operation of the remainder of the system. Thus, one optical fiber distribution configuration is useful in both absorption and luminescent sensors.

Figure 2:
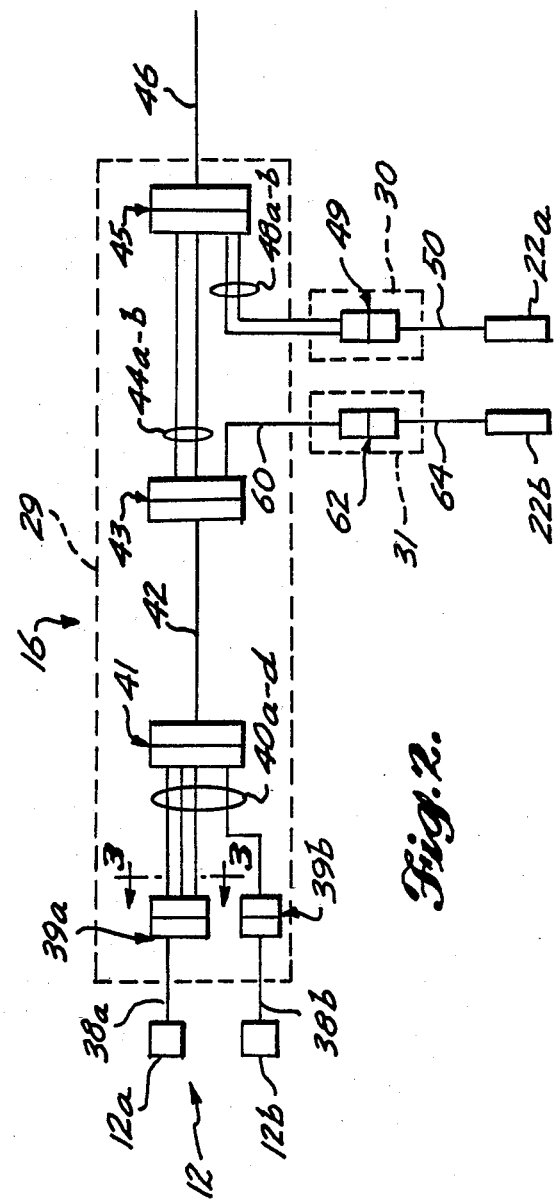
FIG. 2 is a schematic diagram of an optical fiber distribution system in accordance with the invention.

As illustrated in FIG. 2, one preferred embodiment of the optical distribution system 16 suitable for use with an absorption sensor includes three sections: mixed-signal component 29; indicator component 30; and comparison component 31. The mixed-signal component couples measuring and reference signals to produce a mixed signal, transmits the mixed signal to the sensor tip 17, and transmits an indicator signal back from the sensor tip to the distribution system. The indicator component 30 transmits the indicator signal from the mixed-signal component to the indicator-signal detector 22(a) of the signal-measuring component. The comparison component 31 transmits a mixed signal from the mixed-signal component to the comparison-signal detector 22(b) of the signal-measuring component.

The components preferably include lengths of plastic optical fiber and fiber connector pairs. In one preferred system, two diameters of fibers are used. The larger diameter fiber is approximately twice the diameter of the smaller fiber. Suitable diameters for the fibers are 250 $\mu$m and 114 $\mu$m measured across the fiber outer claddings. The fiber connections of the present invention (discussed below) ensure that a signal of predictable intensity is transmitted between the fibers.

The mixed-signal component 29 receives the measuring and reference signal inputs from the signal-generating component 12, which preferably includes a first signal source 12(a) and a second signal source 12(b). Suitable signal sources for pH/$PCO_2$ sensors utilizing a phenol red based quenching-sensitive composition and $PO_2$ sensors utilizing a porphyrin based phosphorescent-sensitive composition, are green 12(a) and red 12(b) L.E.D.s for generating measuring and reference signals, respectively. Input fibers 38(a) and 38(b) carry the signals from the signal sources to dividing connectors 39(a) and 39(b), respectively. Input fibers 38(a) and 38(b) are fibers of the larger diameter. One end of each fiber 38 is placed in abutting relation to one of the L.E.D.s during operation, such that the fiber cross-sectional faces are in complete contact with the L.E.D.s. Thus, the intensities of the signal inputs are equal to the intensities of the L.E.D.s across the fiber cross-sectional areas. The amount of the signal being received from each L.E.D. is thus dictated by the input fiber diameter and the effective numerical aperture of the fiber. The other ends of the input fibers are connected to dividing connectors 39(a) and 39(b).

The measuring and reference signals ae divided into intermediate signals in order to establish a ratio between the measuring and reference signals in the system. In one embodiment, the division is performed by connecting input fiber 38(a) to dividing fibers 40(a-c) which are fibers of the smaller diameter, and connecting input fiber 38(b) to dividing fiber 40(d) which is also a smaller diameter fiber. By this division of the input signals during operation, the ratio between the amount of measuring and reference signals being carried by the optical distribution system is known to be 3:1. By utilizing this dividing component, the intensity of the measuring signal transmitted through the distribution system may be maximized. This signal maximization provides for more accurate monitoring results. The intensity of the measuring signal that is transmitted is bounded by the necessity of transmitting a reference signal of adequate intensity to allow for accurate system operation monitoring.

Figure 3:
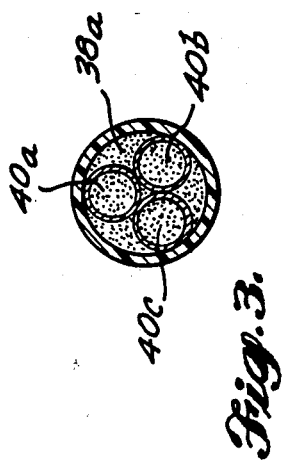
FIG. 3 is a cross-sectional view of a fiber connection in accordance with the present invention.

With reference to FIG. 3, the ends of dividing fibers 40(a-c) connect with the end of input fiber 38(a) at dividing connector 39(a) so that the ends of dividing fibers 40(a-c) are completely subtended by the end of input fiber 38(a). The connection thus ensures that no signal reduction occurs at dividing connector 39(a) due to a portion of any dividing fiber 40(a-c) extending beyond the circumference of input fiber 38(a). Such a misalignment results in a signal of unpredictable intensity being transmitted along the misaligned fibers during operation. In each of the other fiber connectors in the distribution system, the fiber ends are similarly aligned so that the end of the smaller diameter fiber is subtended by the end of the larger diameter fiber. In this manner, the amount of signal transferred at each fiber connection is predictable based on the fiber diameters. The optical fiber connections in the distribution system are preferably established by standard SMA butt-coupled connector pairs. For example, input fiber 38(a) is connected to dividing fibers 40(a-c) by the joining of a pair of connectors into which the fiber ends have been threaded and secured. Fibers of different diameters are connected in this manner. Each connector pair is sized to securely hold the fibers in abutting relationship.

In order to mix the measuring and reference signals into a single mixed signal, dividing fibers 40(a-d) are connected by mixing connector 41 in abutting relationship to mixing fiber 42 which is a fiber of the larger diameter. Mixing fiber 42 is of adequate length to evenly distribute the measuring and reference signals within the fiber. This length requirement ensures that a sample signal obtained at any point along the cross-sectional face of the end of fiber 42 opposite the mixing connector ("remote end") will include proportions of measuring and reference signals equivalent to the ratio in the total signal transmitted by the fiber, i.e., a 3:1 ratio in this embodiment.

During operation, a portion of the mixed signal from mixing fiber 42 is routed along transmitting fibers 44(a) and (b). Transmitting fibers 44 are fibers of the smaller diameter and are connected to the mixing fiber at transmitting connection 43.

The tip connector 45 connects transmitting fibers 44 to tip fiber 46. Tip fiber 46 is preferably a fiber of the larger diameter. The opposite end of the tip fiber 46 is connectable to the sensor tip or to other fibers intermediately positioned relative to the tip. The tip fiber 46 is connectable to any number of sensor tips by connecting devices such as the butt-coupled connector pairs described above. Alternatively, the sensor tip fiber may be directly connected by the tip connector to the transmitting fibers. Since the characteristics of the sensor tip, i.e., the analyte-sensitive composition in the tip, define the analyte to be monitored, the distribution system can be used for a variety of sensor applications.

The indicator component 30 is connected to tip fiber 46 at tip connector 45. The indicator component includes indicator fibers 48, indicator connector 49, and indicator-output fiber 50. During operation, a portion of the signals traveling away from the sensor tip through tip fiber 46 are passed to the indicator fibers 48(a) and 48(b), which are fibers of the smaller diameter. As is the case with most fiber connections, a portion of the mixed signal passing through tip connector 45 towards the sensor tip is reflected back into the transmitting and indicator fibers due to connector characteristics such as changes in the index of refraction across the connecting space. These reflected signals are transmitted along indicator fibers 48 into the indicator component. Since the reflected signals are of the same wavelength as the indicator signals, they must be differentiated from the indicator signals, otherwise the intensity of the indicator signals will be increased by the addition of the reflected signals. The tip connector 45, by connecting tip fiber 46 and indicator fibers 48 in the manner discussed with reference to FIG. 3, reduces the effects of the reflection at the connector. Reflected and indicator signal differentiation is also done by controlling the monitoring process, i.e., controlling the quantity of the signal passed through the system and the timing for the transmitting/measuring processes. This control is a function of the microcomputer 20.

Indicator fibers 48 are connected to indicator-output fiber 50, preferably a fiber of the larger diameter, through indicator connector 49. Indicator-output fiber 50 is directly connected to the indicator-signal detector 22(a).

A portion of the mixed signal is routed from mixing fiber 42 to comparison component 31. The comparison component includes comparison fiber 60, comparison connector 62, and comparison-output fiber 64. The comparison fiber 60 is connected to the mixing fiber 42 by transmitting connector 41 and to the comparison-output fiber 62 by comparison connector 62. Comparison fiber 60 is a fiber of the smaller diameter and comparison-output fiber 64 is a fiber of the larger diameter. The comparison-output fiber 64 is connected to the comparison-signal detector 22(b).

In the preferred embodiment described above, about twenty-five percent of the total mixed signal at transmitting connector 43 is channeled to the comparison-signal detector 22(b) through comparison component 31. Approximately fifty percent of the total mixed signal at transmitting connector 43 is channeled through transmitting fibers 44. Finally, approximately 50 percent of the indicator signal at tip connector 45 is channeled to the indicator-signal detector 22(a) through indicator component 30.

In one preferred mode of operation, a measuring signal is generated at signal generator 12(a) at specific time intervals to provide analyte concentration readings. The readings for pH and $PCO_2$ are obtained by comparing the intensity of the measuring signal wavelength band of the mixed signal with the intensity of the measuring signal wavelength band of the indicator signal.

A reference signal is generated at signal generator 12(b) at specific time intervals in order to perform checks on the distribution system operation. Because the red light is a reference light for sensors using a phenol red based composition, the change of intensity of the reference signal as it is transmitted from the signal-generating component to the signal-measuring component is predictable based on the known reductions at the fiber connections and at the sensor tip. If the intensity of the reference signal received at the indicator component is not as expected when compared to the intensity of the reference signal received at the comparison component, it is an indication that a malfunction, i.e., fiber break or misconnection, has occurred within the distribution system. This further indicates that the measuring signals indicative of analyte concentration may be subject to the same malfunction.

In an alternative use of the invention, the distribution system is connected to a sensor tip in a luminescent sensor system. In a luminescent sensor system, the wavelength of the emitted signal is of a different wavelength than the measuring signal used to excite the indicator molecule. To monitor the presence of the analyte, the time decay of the emitted signal is measured. In this embodiment, the comparison section 31 of the distribution system is not utilized. However, the presence of the comparison section of the distribution system does not detract from the performance of the distribution system in the luminescent sensor system. Additionally, the reference signal is not necessary in order to monitor overall system operation.

The optical fibers used in the described embodiments of the optical fiber distribution system are preferably plastic fibers for ease of handling. Other types of optical fibers, such as glass, are also suitable for the present invention.

When the end of the smaller diameter fiber is completely subtended by the end of a larger diameter fiber, then the loss experienced as the signal travels from the larger diameter fiber to the smaller diameter fiber is:

Area Ratio Loss = 10 Log [(small diameter)/(large diameter)]$^2$

By utilizing these known losses at the fiber connections, the optical distribution system is modifiable and the signal transfer at each connector is determinable so that the system operation is predictable.

Figure 4:
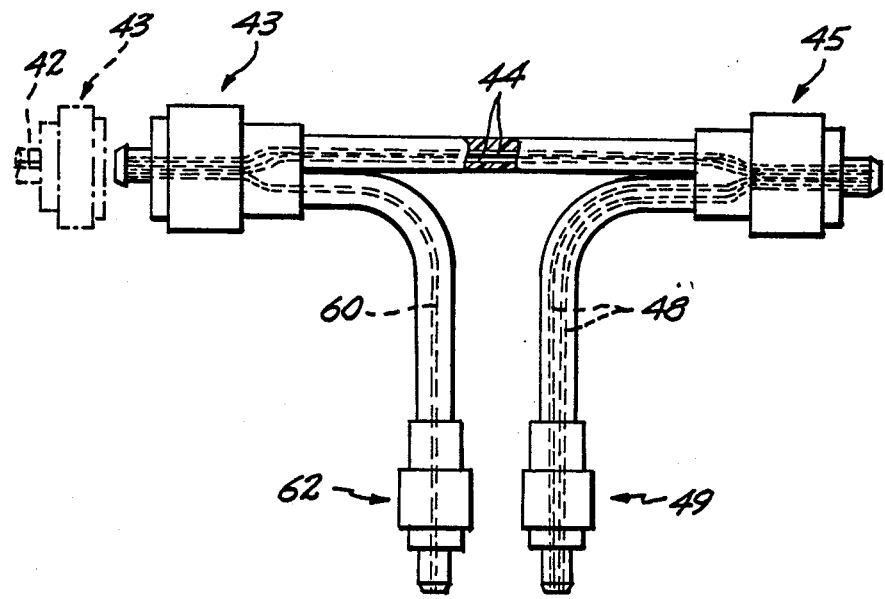
FIG. 4 is a pictorial diagram of a portion of the optical fiber distribution system in accordance with the present invention with a partial cut-away to show one length of optical fiber.

With reference to FIG. 4, a portion of the optical distribution system as it would appear in actual use has the optical fibers encased in polyvinyl chloride (P.V.C.) casing for protection. One half of each butt-coupler pair of the transmitting connector 43, tip connector 45, comparison connector 62 and indicator connector 49 is shown. Thus, for example, the other half of transmitting connector 43, shown in reference, is an SMA connector carrying mixing fiber 42. The connector shown in reference is attached to the illustrated connector to complete mixing connector 43. The distribution system made in this manner can easily be handled without damaging the optical fibers or affecting the integrity of the optical connections.

While preferred embodiments of the invention have been illustrated and described, it will be appreciated that various changes can be made therein without departing from the spirit and scope of the invention. For example, other fiber dimensions are suitable for use if signal intensity requirements dictate. Other optical fiber couplers that provide known and consistent coupling qualities can be used.

One alternative embodiment of the distribution system utilizes more than two distinct signal sources. For example, a third signal source generates a distinct reference signal. At least one dividing fiber is connected to the signal-generating component in order to receive an intermediate signal corresponding in wavelength to the third signal wavelength. The indicator signal corresponding in wavelength to the third signal is utilized as a second system operation indicator. The relationship between the two distinct reference signals provides information related to the system's overall operation. Similarly, additional signals for measuring could be transmitted through the distribution system. The ratio between the various signals transmitted through the system is controlled by the configuration of the dividing connector and fibers.

The embodiments of the invention in which an exclusive property or privilege is claimed are defined as follows:

1. A distribution system for a sensor that utilizes an analyte-sensitive indicator molecule to monitor the concentration of an analyte, the sensor having: a signal-generating component for producing first and second optical signals of distinct wavelengths, the first signal wavelength being such that the signal intensity is altered by the indicator molecule in proportion to the presence of the analyte, the second signal wavelength being such that the intensity of the signal is predictably altered by the indicator molecule so that the intensity of the returned signal is predictable; a single-fiber sensor tip that includes the indicator molecule; and a signal-measuring component for receiving signals from the distribution system, the distribution system comprising:

lengths of optical fiber of first and second diameters, said second diameter being larger than said first diameter;

a dividing connector for connecting at least three intermediate fibers of said first diameter to the signal-generating component to thereby receive intermediate signals, at least one intermediate signal corresponding to the wavelength of the first signal and one intermediate signal corresponding to the wavelength of the second signal;

a mixing connector for connecting a mixing fiber of said second diameter to said intermediate fibers to thereby receive said intermediate signals and blend them into a single mixed signal, said mixing fiber being of a suitable length to mix the first and second signals into a single mixed signal distributed uniformly across said mixing fiber;

a transmitting connector for connecting a transmitting fiber of said first diameter to said mixing fiber to thereby receive a portion of said mixed signal; and a tip connector for connecting said transmitting fiber to the sensor tip fiber to thereby transmit said mixed signal to the sensor tip, and for connecting an indicator fiber of said first diameter to the sensor tip to thereby transmit a portion of the resulting indicator signal returned from the sensor tip to the signal-measuring component, whereby the intensity of said intermediate signals corresponding to the first signal is maximized at the dividing connector, the intensity of said intermediate signals corresponding to the first signal being bounded by the transmission of intermediate signals corresponding to the second signal of adequate intensity such that the intensity of the indicator signal of a wavelength corresponding to the wavelength of the second signal received by the signal-measuring component is suitable for monitoring the operation of the distribution system.

2. The distribution system as claimed in claim 1, wherein said dividing connector, said mixing connector, said transmitting connector, and said tip connector each includes a butt-coupler pair.

3. The distribution system as claimed in claim 1, wherein said dividing connector connects three intermediate fibers to the signal-generating component to thereby receive signals of the first signal wavelength and connects one intermediate fiber to the signal-generating component to thereby receive signals of the second signal wavelength.

4. The distribution system as claimed in claim 3, wherein said transmitting connector connects a plurality of said transmitting fibers to said mixing fiber, and wherein said tip connector connects a plurality of indicator fibers to the sensor tip.

5. The distribution system as claimed in claim 1, wherein the relationship of said first diameter relative to said second diameter, and the configurations of said dividing connector, said mixing connector, said transmitting connector, and said tip connector, are such that at each connector where a fiber of said first diameter is connected to a fiber of said second diameter, the fiber of said second diameter completely subtends the fiber of said first diameter.

6. The optical fiber distribution system as claimed in claim 1, wherein said optical fibers are encased in polyvinyl chloride casing.

7. The optical fiber distribution system as claimed in claim 1, wherein said transmitting connector connects a comparison fiber of said first diameter to said mixing fiber to thereby transmit a portion of said mixed signal to the signal-measuring component.

8. The distribution system as claimed in claim 7, wherein said dividing connector, said mixing connector, said transmitting connector, and said tip connector each includes a butt-coupler pair.

9. The distribution system as claimed in claim 7, wherein said dividing connector connects three intermediate fibers to the signal-generating component to thereby receive signals of the first signal wavelength and connects one intermediate fiber to the signal-generating component to thereby receive signals of the second signal wavelength.

10. The distribution system as claimed in claim 7, wherein the relationship of said first diameter to said second diameter, and the configurations of said dividing connector, said mixing connector, said transmitting connector, and said tip connector, are such that at each connector where a fiber of said first diameter is connected to a fiber of said second diameter, the fiber of said second diameter completely subtends the fiber of said first diameter.

11. The optical fiber distribution system as claimed in claim 7, wherein said optical fibers are encased in polyvinyl chloride casing.

12. The distribution system as claimed in claim 1, wherein the diameter of said mixing fiber is substantially equal to the diameter of the sensor tip fiber.

13. A distribution system for an environmental parameter measuring sensor, the sensor having: a single-fiber sensor tip that includes means for altering a light signal in accordance with the presence of the environmental parameter to be measured; a signal-generating component for producing first and second optical signals of distinct wavelengths, the first signal wavelength being such that the signal intensity is altered at the sensor tip in proportion to the presence of the environmental parameter, the second signal wavelength being such that the intensity of the signal is predictably altered at the sensor tip; and a signal-measuring component for receiving signals from the distribution system, the distribution system comprising:

a plurality of lengths of optical fiber, at least some of said lengths connected in light communicating relationship by abutting the ends thereof, the relationship of the diameters of said abutting optical fibers being such that whenever a group of two or more fibers is connected to a single fiber, the end of said single fiber completely subtends the end of the group of fibers;

a dividing connector for connecting at least three intermediate fibers to the signal-generating component to thereby receive intermediate signals, at least one intermediate signal corresponding to the wavelength of the first signal and one intermediate signal corresponding to the wavelength of the second signal;

a mixing connector for connecting a mixing fiber to said intermediate fibers to thereby receive said intermediate signals and blend them into a single mixed signal, said mixing fiber being of a suitable length to mix the first and second signals into a single mixed signal distributed uniformly across said mixing fiber;

a transmitting connector for connecting a transmitting fiber to said mixing fiber to thereby receive a portion of said mixed signal;

a tip connector for connecting said transmitting fiber and an indicator fiber to tip fiber means for transmitting said mixed signal to the sensor tip and for transmitting a portion of the resulting indicator signal returned from the sensor tip to said indicator fiber, whereby the signal returned from the sensor tip is transmitted to the signal-measuring component via said indicator fiber and the intensity of said intermediate signals corresponding to the first signal is maximized at the dividing connector, the intensity of said intermediate signals corresponding to the first signal being bounded by the transmission of intermediate signals corresponding to the second signal of adequate intensity such that the intensity of the indicator signal of a wavelength corresponding to the wavelength of the second signal received by the signal-measuring component is suitable for monitoring the operation of the distribution system.

14. The distribution system as claimed in claim 13, wherein said tip fiber means includes the single-fiber of the sensor tip.

15. The distribution system as claimed in claim 13, wherein said tip fiber means includes an extension fiber, one end of which is connected to said transmitting fiber and said indicator fiber via said tip connector.

16. The distribution system as claimed in claim 13, wherein said transmitting connector further connects a comparison fiber to said mixing fiber to thereby transmit a portion of said mixed signal to the signal-measuring component.

17. A method for distributing signals in an environmental parameter measuring sensor, the sensor having: a single-fiber sensor tip that includes means for altering a light signal in accordance with the presence of the environmental parameter to be measured; a signal-generating component for producing first and second optical signals of distinct wavelengths, the first signal wavelength being such that the signal intensity is altered at the sensor tip in proportion to the presence of the environmental parameter, the second signal wavelength being such that the intensity of the signal is predictably altered at the sensor tip; a signal-measuring component for receiving signals from the distribution system; a plurality lengths of optical fibers, at least some of said lengths connected in light communicating relationship by abutting the ends thereof, the relationships of the diameters of said connected optical fibers being such that whenever a group of two or more fibers is connected to a single fiber, the end of said single fiber completely subtends the end of the group of fibers, said method comprising the steps of:

dividing the first and second signals into intermediate signals by connecting at least three intermediate fibers to the signal-generating component such that at least one intermediate signal corresponds to the wavelength of the first signal and one intermediate signal corresponds to the wavelength of the second signal;

mixing said intermediate signals into a mixed signal by connecting a mixing fiber to said intermediate fibers to thereby receive said intermediate signals and blend them into a single mixed signal, said mixing fiber being of a suitable length to mix the first and second signals into a single mixed signal distributed uniformly across said mixing fiber;

transmitting a portion of said mixed signal along a transmitting fiber by connecting said transmitting fiber to said mixing fiber;

transmitting a portion of said mixed signal along a comparison fiber by connecting said comparison fiber to said mixing fiber;

transmitting said mixed signal from said transmitting fiber to the sensor tip by connecting said transmitting fiber to the tip fiber means; and transmitting a portion of the resulting indicator signal returned from the sensor tip along an indicator fiber by connecting an indicator fiber to the tip fiber means, whereby the signal returned from the sensor tip is transmitted to the signal measuring component via said indicator fiber and the intensity of said intermediate signals corresponding to the first signal is maximized at the dividing connector, the intensity of said intermediate signals corresponding to the wavelength of the first signal being bounded by the transmission of intermediate signals corresponding to the second signal of adequate intensity such that the intensity of the indicator signal of a wavelength corresponding to the wavelength of the second signal received by the signal-measuring component is suitable for monitoring the operation of the distribution system.

18. A method for distributing signals in a sensor that utilizes an analyte-sensitive indicator molecule to monitor the concentration of an analyte, the sensor having: a signal-generating component for producing first and second optical signals of distinct wavelengths, the first signal wavelength being such that the signal intensity is altered by the indicator molecule in proportion to the presence of the analyte, the second signal wavelength being such that the intensity of the signal is predictably altered by the indicator molecule; a single-fiber sensor tip that includes the indicator molecule; a signal-measuring component for receiving signals from the distribution system; and a plurality of optical fibers of first and second diameters, the second diameter being larger than the first diameter, said method comprising the steps of:

dividing the first and second signals into intermediate signals by connecting at least three intermediate fibers of the first diameter to the signal-generating component such that at least one intermediate signal corresponds to the wavelength of the first signal and one intermediate signal corresponds to the wavelength of the second signal;

mixing said intermediate signals into a mixed signal by connecting a mixing fiber of the second diameter to said intermediate fibers to thereby receive said intermediate signals and blend them into a single mixed signal, said mixing fiber being of a suitable length to mix the first and second signals into a single mixed signal distributed uniformly across said mixing fiber;

transmitting a portion of said mixed signal along a transmitting fiber of the first diameter by connecting said transmitting fiber to said mixing fiber;

transmitting a portion of said mixed signal along a comparison fiber of the first diameter by connecting said comparison fiber to said mixing fiber;

transmitting said mixed signal from said transmitting fiber to the sensor tip by connecting said transmitting fiber to the sensor tip fiber; and transmitting a portion of the resulting indicator signal returned from the sensor tip to the signal-measuring component by connecting an indicator fiber of the first diameter to the sensor tip, whereby the intensity of said intermediate signals corresponding to the first signal is maximized at the dividing connector, the intensity of said intermediate signals corresponding to the wavelength of the first signal being bounded by the transmission of intermediate signals corresponding to the second signal of adequate intensity such that the intensity of the indicator signal of a wavelength corresponding to the wavelength of the second signal received by the signal-measuring component is suitable for monitoring the operation of the distribution system.

* * * * *